US009322644B2

(12) United States Patent
Weinhold

(10) Patent No.: US 9,322,644 B2
(45) Date of Patent: Apr. 26, 2016

(54) METHOD AND APPARATUS FOR THE EXAMINATION OF AN OBJECT

(76) Inventor: Wolfgang Weinhold, Wurzburg (DE)

( * ) Notice: Subject to any disclaimer, the term of this patent is extended or adjusted under 35 U.S.C. 154(b) by 0 days.

(21) Appl. No.: 12/500,064

(22) Filed: Jul. 9, 2009

(65) Prior Publication Data

US 2010/0033715 A1  Feb. 11, 2010

Related U.S. Application Data

(63) Continuation of application No. PCT/DE2007/002316, filed on Dec. 28, 2007, now abandoned.

(51) Int. Cl.
*G01N 21/00* (2006.01)
*G01B 11/30* (2006.01)
*G01N 21/27* (2006.01)
*G01N 21/47* (2006.01)

(52) U.S. Cl.
CPC ............ *G01B 11/303* (2013.01); *G01N 21/274* (2013.01); *G01N 21/4738* (2013.01)

(58) Field of Classification Search
CPC ...... G01B 11/303; G01B 11/24; G01B 11/25; G01N 21/00
USPC ........... 356/237.2–237.5, 445, 446, 448, 600, 356/601; 250/341.8
See application file for complete search history.

(56) References Cited

U.S. PATENT DOCUMENTS

| 5,612,782 | A | 3/1997 | Keraenen | |
| 5,905,570 | A | 5/1999 | White | |
| 5,963,333 | A | 10/1999 | Walowit | |
| 6,603,551 | B2 * | 8/2003 | Mestha et al. | 356/402 |
| 6,809,855 | B2 * | 10/2004 | Hubble et al. | 359/320 |
| 6,915,565 | B2 * | 7/2005 | Isogai et al. | 29/833 |
| 7,006,229 | B2 * | 2/2006 | Sperling et al. | 356/445 |
| 7,227,648 | B2 * | 6/2007 | Weinhold | 356/601 |
| 7,276,719 | B2 * | 10/2007 | Schwarz | 250/559.36 |
| 7,551,283 | B2 * | 6/2009 | Obinata | 356/429 |

(Continued)

FOREIGN PATENT DOCUMENTS

| DE | 3540288 C2 | 10/1988 |
| DE | 4123916 C2 | 4/1998 |
| DE | 19716264 A1 | 10/1998 |

(Continued)

*Primary Examiner* — Tarifur Chowdhury
*Assistant Examiner* — Isiaka Akanbi
(74) *Attorney, Agent, or Firm* — Andrew F. Young, Esq.; Lackenbach Siegel, LLP

(57) ABSTRACT

The invention relates to a method and an apparatus for examining an object, particularly in terms of the surface morphology thereof. Said apparatus comprises a transportable housing which can be placed, especially by hand, above the surface segment of the object that is to be examined, and at least three light sources, the optical beam axes of which extend at a slanted angle of incidence relative to the surface segment that is to be examined. The light sources are disposed inside the housing and can illuminate the surface segment that is to be examined through an illumination aperture in the housing. The apparatus further comprises at least one light sensor for detecting the light reflected on the surface segment that is to be examined and a control and evaluation unit which is connected to the light sources and the light sensor. The light sources are arranged such that the optical beam axes thereof extend on different, non-parallel reference planes.

28 Claims, 2 Drawing Sheets

(56) References Cited

U.S. PATENT DOCUMENTS

| | | | |
|---|---|---|---|
| 7,777,897 B1 * | 8/2010 | Gibbons | 356/601 |
| 2001/0017698 A1 | 8/2001 | Thakur | |

FOREIGN PATENT DOCUMENTS

| | | |
|---|---|---|
| DE | 19716228 C2 | 2/2002 |
| DE | 103 19 543 | 11/2004 |
| DE | 10319543 A1 | 11/2004 |
| DE | 10336493 A1 | 3/2005 |
| WO | 02/090952 A1 | 11/2002 |
| WO | WO 02/090952 | 11/2002 |
| WO | 03/010521 A1 | 2/2003 |
| WO | WO 03/010521 | 2/2003 |
| WO | 2004/051320 A2 | 6/2004 |
| WO | WO 2004/051320 | 6/2004 |

* cited by examiner

METHOD AND APPARATUS FOR THE EXAMINATION OF AN OBJECT

STATEMENT OF RELATED CASES

Pursuant to 35 U.S.C. 111(a), the instant application is a continuation of International Application PCT/DE2007/002316, with an international filing date of Dec. 28, 2007, now abandoned.

The invention relates to an apparatus for the examination of an object, in particular in terms of its surface morphology, according to the preamble of claim 1. Additionally, the invention relates to a method whereby the method is carried out according to the teaching of the main claim of the method.

Methods and apparatuses which examine the surface morphology of objects with the aid of optical resources are already known. Thus rays of light or oblique light can be used to illuminate surfaces from an oblique or flat angle, and in a simple manner localize and quantify, for example, soil particles lying on the surface, unevenness, rough spots, processing traces and similar. This is based on the fact that, depending on the characteristics of such deviations compared to the expected morphology, more or less intensely bright or dark spots are formed, for example due to illuminated and shaded edges, which in turn allows conclusions to be drawn about the three-dimensional surface morphology. This type of procedure is adequately known under the term ray of light or oblique light procedure, for example from DE 197 16 264 A1. The corresponding effect is also known as shading or shadow plastic. Generally speaking there is a functional relationship between the angle of incidence of the light, the three-dimensional orientation and the position of a sub-area, especially its inclination and height, and the angle of emergence of the reflected light. The reflected light is captured by a light sensor, for example a line or matrix CCD camera, as a measured value, and then undergoes digital image processing. This procedure is particularly well-suited for point-shaped, linear or frequently re-occurring surface deviations, such as soiling and scratches for example.

DE 35 40 288 C2 describes an optical inspection system for the inspection of soldered points on printed circuit boards. In this, light is directed at the soldered points and the reflected light is captured by a detection unit oriented at a 90° angle to the soldered point.

DE 41 23 916 C2 describes a method and an apparatus for identifying and classifying surface qualities and defects of an object under inspection using dynamic illumination.

DE 197 16 228 C2 describes a method and an apparatus for checking a surface, by means of which scratches and soiling in particular can be detected. Here, the surface to be checked is illuminated by light beams arranged in a pattern.

DE 103 19 543 A1 describes a method and an apparatus for checking a surface, in which a material which absorbs the light beams is disposed above the light sources.

DE 103 36 493 A1 describes a method and an apparatus for checking a surface, which has two light sources, each of which has a beam detector unit.

The prior art methods and apparatuses have, however, the disadvantage that they are unsatisfactory for the detection of the features of surfaces which have a preferred orientation. In sheet metal and paper manufacture, for example, the surfaces are produced with a preferred orientation, which has an important effect on the surface morphology. This preferred orientation can, however, not be detected in a satisfactory way by the known methods and apparatuses. In addition, the calibration of the prior art apparatuses is extremely complex, and often leads to inaccurate measurement results.

Thus the objective of the present invention is to provide an apparatus of the type specified in the introductory remarks, which facilitates the exact detection of the characteristics of a surface independent of particular preferred orientations. It is additionally the objective of the present invention to suggest a method for the simple and accurate calibration of such apparatuses.

This objective is accomplished by an apparatus according to the feature of claim 1. The objective is further accomplished by the independent main method claim. Advantageous embodiments of the invention are the subject matter of the subordinate claims.

Investigations of known apparatuses for touch-free examination of an object with regard to its surface morphology, as, for example, described in WO 02/090952 A1, have shown that unsatisfactory detection of the surface morphology taking into account preferred orientations results from the fact that the light sources are arranged in such a manner that the optical beam axis with its inclined angle of incidence is arranged in each case in a single reference plane. According to the positioning of this plane of reference relative to the preferred orientation of the surface morphology of the material to be examined, differing results will be thus obtained from the examination. According to the teaching of claim 1, it is therefore envisaged that the at least three light sources are so arranged that their optical beam axes are aligned in reference planes which are different from one another and non-parallel. This ensures that the surface morphology of the preferred orientation is in each case illuminated, independently of the particular positioning of the apparatus, from different directions, so that the measurement results no longer depend on the positioning of the apparatus relative to the preferred orientation.

The angle of incidence of the optical beam axes of the light sources should preferably be in the range of 70° to 10° relative to the surface segment to be inspected.

The reference planes in which the optical beam axes are aligned should be arranged perpendicular to the surface segment to be inspected.

In order that all light sources illuminate in an optimal way the same surface segment, the reference planes should cross each other at a line of intersection. The mid area of the surface segment to be inspected is then defined by this line of intersection. In this, it is particularly advantageous if the optical beam axes of the light sources cross each other at a crossover point on the surface segment to be inspected, in order to concentrate the light emitted by the light sources on the surface segment to be inspected.

The arrangement of the at least three reference planes of the at least three light sources relative to each other is in principle optional. In order to ensure that the illumination of the surface segment to be inspected is as uniform as possible, it is particularly advantageous if the reference planes are aligned at equal angles with respect to one another. This means, in other words, that when three light sources are used, with three corresponding reference planes, there is an angle of 120° in each case between the different reference planes.

Particularly exact measurements of the surface morphology, based on the color or grayscale information from the light reflected from the surface, are achieved if the light sources illuminate the surface segment to be inspected with light whose optical paths are substantially parallelized.

Light sources for generating immediately parallelized light, for example lasers, are relatively expensive. In order to reduce the manufacturing costs in this respect, it is thus particularly advantageous to arrange an optical element between the illuminant of the light source, for example an LED, and the surface segment to be inspected, by means of which the light radiated from the illuminant can be parallelized. As optical elements, it is possible for example to use lenses, in particular Fresnel lenses, or alternatively lens systems comprising multiple lenses.

The light sensor for detecting the light reflected from the surface should preferably be aligned with its optical axis perpendicular relative to the surface segment to be inspected.

In this it is particularly advantageous if the optical axis of the light sensor and the line of intersection of the reference planes are coaxial.

The choice of color of the light emitted from the light sources depends on the use to which the invention is put in each case. For example, all light sources can emit white light. According to a preferred embodiment, it is envisaged that each light source emits light of a different color, whereby the light sensor can detect the different light colors from the light sources separately from each other, in particular also when the light sources radiate the light simultaneously. As a result it is thus possible to illuminate the surface segment to be inspected with, for example, three colors of light from different directions, and to capture the reflected light in each case by means of the light sensor. Because a different color is allocated to the incident light from each direction, this can be appropriately taken into account and differentiated when the light measurements are evaluated.

In order additionally to capture visually the surface segment to be inspected, it is particularly advantageous if the apparatus also has one or more overall light sources, to achieve overall illumination of the surface segment to be inspected. In this case, the same light sensor that is used to capture the topographical impression is also used to capture the visual impression. As a result it thereby becomes possible to inspect the surface segment simultaneously, both topographically and with regard to its visual impression, without relocating the measurement apparatus. In this manner, the measurement data captured by the overall illumination, and the measurement data from the topographical inspection, in which the same surface segment is illuminated by means of the light sources arranged at inclined incident angles, can be related to each other, and further results can be derived from the investigation. This is because the surface segment subjected to topographical investigation corresponds to the surface segment of which a visual impression is obtained, and they are captured with the same dimensions, at the same scale, and at the same resolution, by the same light sensor. The two measurements differ only with respect to the type of surface illumination.

The characteristics of the overall light source are in principle optional. Particularly simple designs are possible if the same illuminant is used for the overall light source as for the other light sources. However, the different light sources and the overall light source must then be energized successively, in order that the signals are not superimposed. If the overall light source has a different illumination characteristic, in particular a different light color, from the three light sources which are arranged at inclined incident angles, it becomes possible to energize the overall light source simultaneously with the other light sources, since the different light sources can be differentially evaluated based on their different illumination characteristics.

Handling the apparatus according to the invention is particularly easy if the housing is constructed in the manner of a handheld device. The person that operates this handheld device can then move it manually over the surface to be inspected, and position it suitably.

With the exception of the illumination apertures, the handheld device should be largely impermeable to light, in order to hinder the penetration of interfering light.

To enable the easy positioning of the handheld device in a defined relative position on the surface segment to be inspected, it is particularly advantageous if the handheld device is provided with a defined, in particular flat, support surface. By use of this support surface, the handheld device can then be placed at a defined location on the surface segment to be inspected, and thereby definitely positioned. In particular, a defined angle of illumination and a defined illumination distance can be easily maintained.

According to a preferred embodiment, the housing of the handheld device has a recess along the side of the support surface. By means of this recess the operator can view the support surface clearly from the side when positioning it, thus simplifying the process of precise positioning.

It is additionally particularly advantageous if the handheld device has at least one, and especially three, flat gripping surfaces, by means of which the operator can guide the handheld device. The ergonomics of using the device are thereby improved. Additionally, the gripping surfaces can serve as an aid to orientation when the handheld device is positioned at a particular relative angle.

The housing can optionally also have positioning aids, for example mechanical locating surfaces, to enable the apparatus to be repeatedly positioned at different times with high accuracy at an identical measurement point on an object to be inspected.

To bring about an additional improvement in its handling, the handheld device can be connected to a second operating unit, for example an industrial computer. Part of the control and evaluation process can be implemented by this second unit, and thus need not performed by the handheld device. The power supply for the hand device can also be implemented via the second operating unit.

An additional improvement in the handling of the apparatus according to the invention is achieved if data is transferred between the handheld device and the second operating unit via a wireless connection. By this means it is possible to dispense with the connecting cable between the handheld device and the operating unit which would otherwise be necessary.

Along with this, the handheld device can contain a power source which does not require a cable, such as a battery, in order to implement the supply of power without the inconvenience of a supply cable.

In order to avoid malfunctions and misuse, a hardware component—a so-called dongle (or copy protection hardware key)—can be installed in the handheld device. This hardware component can then be queried by the part of the control and evaluation process that is implemented on the second user device, as a check for authorization. The functionality of the second user device will then be enabled only in the case of unambiguous identification of an authorized dongle.

Additionally, the handheld device can have one or more displays and/or one or more operating controls, for example switches.

In order to extend its possible applications, at least one backlight source can be attached to the apparatus. By means of this, the surface segment to be inspected can be backlit. The light which passes through the surface is thereby captured by the same light sensor as the reflected light. As a result of this it becomes possible that the surface segment which is inspected topographically and/or visually is at the same time also inspected using backlighting without the need to reposition the measurement apparatus, in order, for example, to detect marbling in paper from a roll. The measurement data obtained using the backlight, and the measurement data from the topographical inspection, in which the same surface segment is illuminated by the light sources arranged at inclined incident angles, can be related to each other by this means, and further results can be derived from the investigation. This is because the surface segment subjected to topographical investigation corresponds to the surface segment inspected using backlight, and they are captured with the same dimensions, at the same scale, and at the same resolution, by the same light sensor. The two measurements differ only with respect to the type of illumination.

The method according to the invention is based on the fundamental consideration that accurate measurement of the surface segment to be inspected requires illumination that is as uniform as possible. However, the more stringent the requirement for uniform illumination, the greater the expense and complexity of the equipment that is required to implement the light sources. Uniform illumination of the surface segment to be inspected is also of great importance when the material to be inspected has a preferred orientation. The method according to the invention serves to minimize the expense and complexity of the equipment in that at least a slight lack of uniformity of the illumination is accepted, but this lack of uniformity is captured as a known disturbance variable and taken account of as a correction value.

Calibration thereby takes place in the following steps:

a) Introduction of a calibration work piece with defined, uniform and known surface attributes.

b) Illumination of a surface segment of the calibration work piece with the light sources that are present.

c) Capture of the light reflected from the surface segment of the calibration work piece with the light sensor.

d) Establishment of the difference value between the actual reflection value measured at the calibration work piece and the expected reflection value based on the known surface attributes of the calibration work piece.

e) Storing of the difference value as a correction value for subsequent inspections. Naturally, multiple difference values can also be calculated, depending on the procedures used.

The type of calibration work piece used is in principle optional. Bright ceramic bodies have proved to be particularly suited to this purpose.

In order to increase the accuracy of the calibration, the surface segment to be inspected can additionally be divided into several sub-areas. A separate correction value for each of these sub-areas can then be calculated by the difference value method, and recorded.

These correction values, of which there will necessarily be a multiplicity, can be stored in a correction matrix, for example an inverse intensity correction matrix.

The calibration can be further extended in a second process step, in that:

a) a calibration work piece with a defined and known height structure, for example an indentation with a known geometry, is introduced. The height structure of the calibration work piece is illuminated by the light sources, and b) the light thus reflected from the height structure is captured by the light sensors.

A correlation factor is subsequently derived from the measured actual reflection value and the known height structure of the calibration work piece, and c) the correlation factor is stored for later inspections.

For the determination of the correlation factor, the height structure of the calibration work piece should if possible be illuminated from different directions, in particular illuminated from three directions, in order again to avoid distortions due to preferred orientations in the material.

According to an additional preferred variant of the method, the visual impression captured by the use of the overall illumination can also be calibrated.

Two embodiments of the invention are shown schematically in the drawings, and are explained below as examples. The drawings show:

Figure 1:
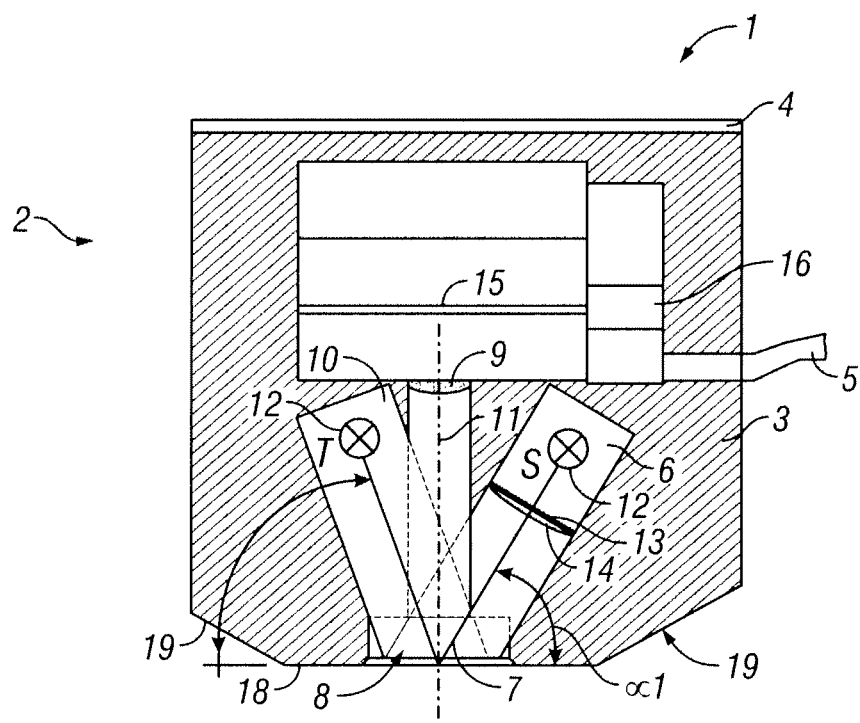
FIG. 1 is a first embodiment of an apparatus according to the invention, in longitudinal section.

In FIG. 1 an apparatus 01 for the touch-free examination of the surface morphology of an object is shown in longitudinal section. Apparatus 01 comprises a transportable housing 02 with a basic body 03 and a housing cover 04. Displays and operating controls may be disposed on the upper side of the housing cover 04.

Housing 02 is designed in the manner of a handheld device, and must be connected via a connecting cable 05 to an industrial computer (not shown) in order to complete apparatus 01. By means of the connecting cable 05, data is exchanged and the power supply to apparatus 01 is implemented. As an alternative, the data connection between housing 02 and the industrial computer can also be implemented by means of wireless data transmission. In this case, apparatus 01 must be provided with its own power source, for example a battery.

In the light-proof basic body 03 of the housing 02, three light sources 06 are installed, which, after the housing 02, with a level support surface 18, is arranged on the surface segment to be inspected, are aligned with their optical beam axes 07 at a defined inclined angle of incidence relative to the surface segment to be inspected. The surface segment to be inspected is thereby arranged below an illumination aperture 08. The light reflected from the surface segment to be inspected is captured by a light sensor 09. The light sensor 09 can thereby be designed for example in the manner of a CCD chip matrix. By the evaluation of the measured values captured by the light sensor 09, the surface morphology of the surface segment to be inspected can be determined. The handheld device 02 has a recess 19 in its housing along the side of the support surface 18, in order to facilitate the positioning of the support surface 18 by the operator.

Figure 2:
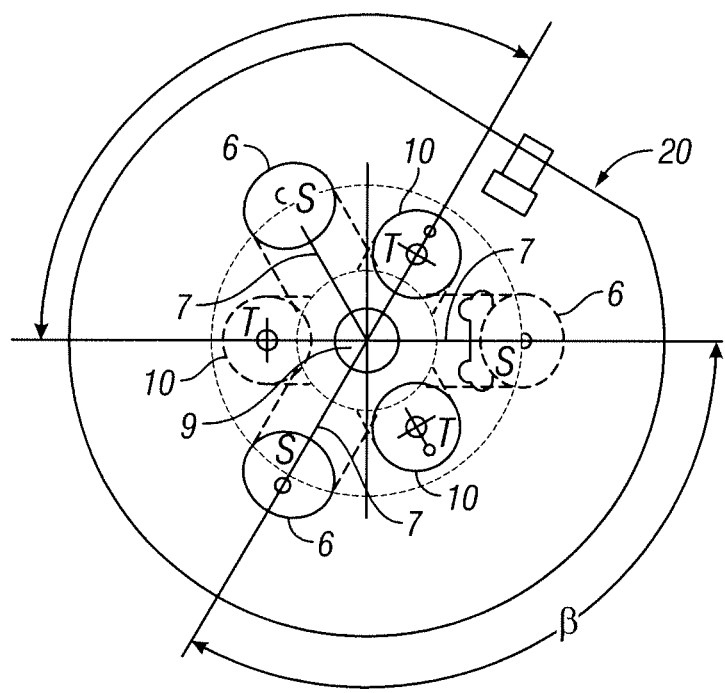
FIG. 2 is the apparatus according to FIG. 1 in cross section.

As can be seen in FIG. 2, the apparatus 01 contains three light sources 06. Apparatus 01 also has three additional light sources 10, which are designed in the manner of overall light sources and together provide overall illumination. The optical beam axes 07 of the three light sources 06 are aligned at an inclined angle of incidence $\alpha$ of approximately 70° relative to the surface segment to be inspected. Additionally the optical beam axes 07 of the three light sources 06 are each aligned in reference planes which are perpendicular to the surface segment to be inspected. These three reference planes are thereby arranged in housing 02 with angles $\beta$ between them of 120° in each case, i.e. at equidistant angles with respect to each other. As a result of this, the reference planes intersect in a line of intersection which is coaxial with the optical axis 11 of the light sensor 09.

In order to be able to radiate parallelized light upon the surface segment to be inspected during measurement, each light sources 06 has a light emitting diode 12 as illuminant, whereby the light radiated from the light emitting diodes 12 passes through a lens system comprising two lenses 13 and 14 to fall on the surface segment to be inspected. In passing through the lenses 13 and 14, the light radiated from the light emitting diode 12 is to a large extent parallelized.

The control system necessary to control the light sources 06, 10, and the light sensor 09, is implemented on an electronic circuit board 15. Also part of this electronic circuit board 15 is a dongle 16, which can be queried as a check on authorization when the handheld device is connected with an industrial computer by means of the connecting cable 05.

In order to facilitate the positioning of the handheld device 02 in a desired orientation, there is a flat gripping surface 20 around the handheld device 02, which can be gripped by the operator's fingers.

Figure 3:
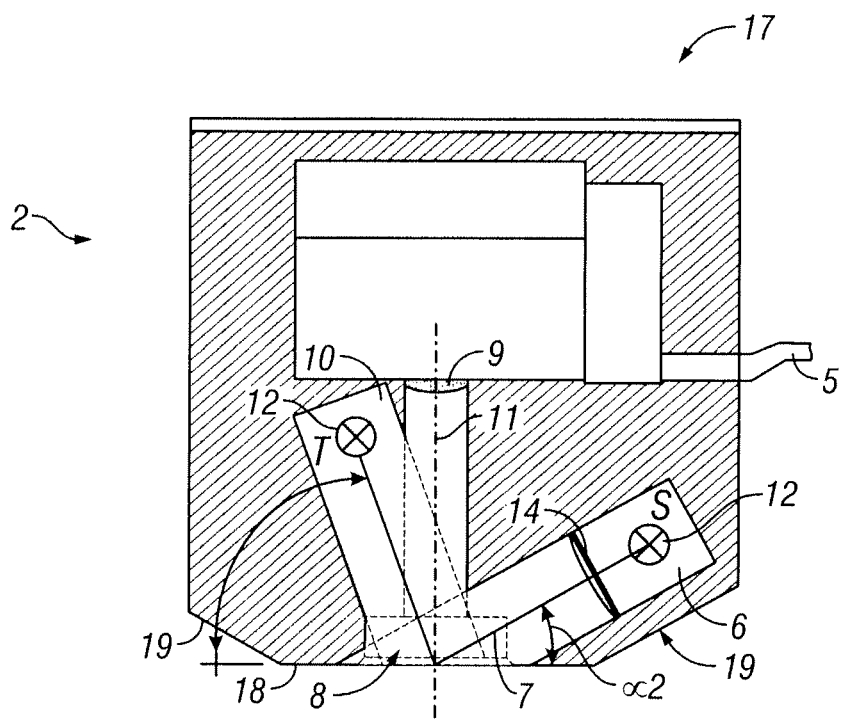
FIG. 3 is a second embodiment of an apparatus according to the invention, in longitudinal section.

In FIG. 3 a second embodiment 17 of an apparatus according to the invention is shown. Apparatus 17 differs from apparatus 01 substantially only with respect to the angle of incidence α, which in the case of apparatus 17 is approximately 30°.

The remaining components of apparatus 17 are essentially identical to those of apparatus 01.

Figure 4:
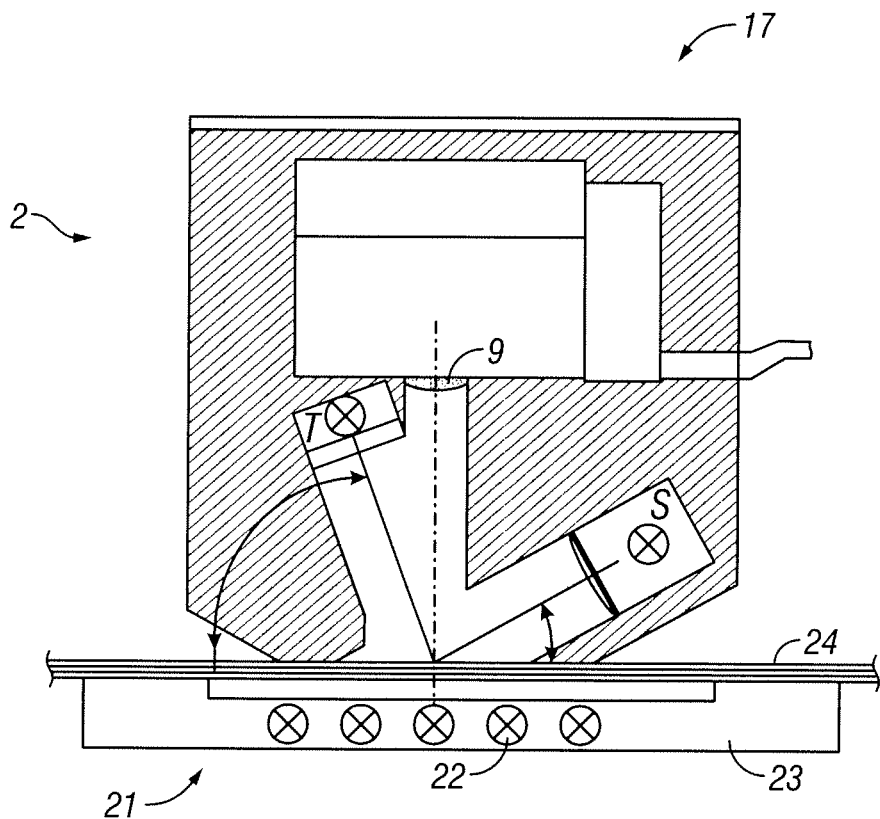
FIG. 4 is the apparatus according to FIG. 2 with an additional backlight source.

In FIG. 4, apparatus 17 is shown with an additional backlight source 21, which is designed in the manner of a transillumination table. Under a transparent plate 22, several illuminants 22 are arranged on a board 23. The object to be examined, namely paper 24 from a roll, is arranged between the backlight source 21 and apparatus 17, so that, in addition to the topographical examination and the capture of the visual impression, a backlit inspection can also be performed.

LIST OF REFERENCE SIGNS

01 apparatus
02 housing
03 basic body of the housing
04 housing cover
05 connecting cable
06 light source
07 optical beam axis
08 illumination aperture
09 light sensor
10 light source (overall illumination)
11 optical axis (light sensor)
12 light emitting diode
13 lens
14 lens
15 electronic circuit board
16 dongle
17 apparatus
18 support surface
19 recess in housing
20 gripping surface
21 backlight source
22 transparent plate
23 board
24 paper

The invention claimed is:

1. An apparatus for the inspection of an object, especially with regard to its surface stature, said apparatus comprising:
   a. a transportable housing manually moveable over an object, the object comprising a surface segment to be inspected and defining an inspection plane thereof;
   b. exactly three light sources having operative illuminants, wherein the three light sources are aligned such that an optical beam axis of each said light source is at an angle relative to the surface segment to be inspected;
   c. wherein the light sources are arranged inside a housing and wherein a light aperture in the housing is operative to allow the surface segment to be illuminated with light from each of said light sources, each of whose optical paths are substantially parallelized;
   d. at least one light sensor for capturing reflected light from the surface segment;
   e. control and evaluation units for coupling the three light sources with the at least one light sensor; and
   f. one or more lenses placed between each said illuminant of each said light source and the surface segment to be inspected, thereby substantially parallelizing light radiated by each said illuminant as it passes through the lenses and is radiated upon the surface segment,
   g. wherein said optical beam axes are aligned in respective reference planes intersecting at a line of intersection that is substantially coaxial with an optical axis of the light sensor; and
   h. wherein each said reference plane is at approximately one hundred twenty degrees (120°) with respect to each other.

2. The apparatus according to claim 1, wherein the optical beam axes of the light sources are aligned at an angle α in the range of 70° to 10° relative to the surface segment to be inspected.

3. The apparatus according to claim 1, wherein the reference planes are aligned perpendicular relative to the surface segment to be inspected.

4. The apparatus according to claim 1, wherein the reference planes cross each other forming a crossover line.

5. The apparatus according to claim 4, wherein the beam axes of the light sources cross at a crossover point on the surface segment to be inspected.

6. The apparatus according to claim 1, wherein each of the illuminants includes a light emitting diode.

7. The apparatus according to claim 1, wherein an optical axis of the light sensor is aligned perpendicular to the surface segment to be inspected.

8. The apparatus according to claim 1, wherein an optical axis of the light sensor is coaxial with the line of intersection of the reference planes.

9. The apparatus according to claim 1, wherein the light sources radiate light in different colours.

10. The apparatus according to claim 1, wherein the light sources radiate different light colours, and the light sensor can effectively detect the different light colours, said light colours being selected from the group consisting of white light, infrared light and ultraviolet light.

11. The apparatus according to claim 1, wherein the apparatus-further comprises an overall light source having a steep incident angle with which an overall illumination is implemented for capturing a visual impression of the inspected surface segment.

12. The apparatus according to claim 11, wherein the overall light source demonstrates a different illumination characteristic to that of the three light sources.

13. The apparatus according to claim 1, wherein the housing forms a handheld device.

14. The apparatus according to claim 13, wherein the handheld device is impermeable to light apart from the light aperture.

15. The apparatus according to claim 13, wherein the handheld device comprises a definite support surface for facilitating precise maneuverability to the exact location of the inspected surface segment.

16. The apparatus according to claim 15, wherein the handheld device comprises a limiter aligned to the support surface.

17. The apparatus according to claim 13, wherein the handheld device is used in conjunction with a second user device, such as an industrial computer, where part of the control and evaluation units and/or a power supply of the handheld device can be implemented by the second device.

18. The apparatus according to claim 1, wherein the apparatus comprises at least one backlight source for allowing illumination of the surface segment to be inspected, said segment illumination being captured by the light sensor.

19. The apparatus according to claim 1, wherein the one or more lenses has a number equaling two lenses.

20. A method for non-contact inspection of an object, particularly with respect to its surface stature, said method comprising the steps of:
   a. providing an object, said object comprising a surface segment to be inspected;
   b. illuminating the surface segment to be inspected with parallelized light by means of three light sources aligned such that an optical beam axis of each said light source is at an angle relative to the surface segment to be inspected, wherein said optical beam axes are aligned in respective reference planes intersecting at a line of intersection that is substantially coaxial with an optical axis of a light sensor, and each said reference plane is at approximately one hundred twenty degrees (120°) with respect to each other;
   c. capturing, by means of a light sensor, light reflected from the surface segment to be inspected, and generating measurement data; and
   d. evaluating, by means of a control and evaluation process, the measurement data;
   e. passing light radiated from each of said light sources through a lens system that includes one or more lenses, thereby operatively parallelizing the light as it passes through the lenses prior to the light being radiated upon the surface segment.

21. The method according to claim 20, wherein calibration is completed before inspection of the surface segment, said calibration comprising the steps of:
   a. introducing a calibration work piece, said calibration work piece comprising a calibration surface segment with defined, uniform and known surface attributes and theoretical reflection values,
   b. illuminating the calibration surface segment with the three light sources,
   c. capturing reflected light from the calibration surface segment with the light sensor, and obtaining actual reflection values,
   d. establishing difference values between the actual reflection values and the theoretical reflection values due to the known surface attributes of the calibration work piece, and
   e. storing the difference values as correction values for successive inspections.

22. The method according to claim 21, wherein the calibration work piece is a bright ceramic body.

23. The method according to claim 21, wherein the surface segment is broken down into sub-segments, where for each sub-segment a separate correction value is established and recorded.

24. The method according to claim 21, wherein the correction values are recorded in a correction matrix.

25. The method according to claim 20, wherein calibration is completed before inspection of the surface segment, said calibration comprising the steps of:
   a. presenting a calibration work piece with defined, uniform and known surface attributes, including a known height value based on a known height structure, said calibration work piece comprising a calibration surface segment,
   b. illuminating the calibration surface segment with the three light sources,
   c. capturing reflected light from the calibration surface segment with the light sensor, and obtaining actual reflection values,
   d. determining a correlation factor between the actual reflection value and the known height value, and
   e. storing the correlation factor for successive inspections.

26. The method according to claim 25, wherein, during the determining of the correlation factor, the height structure of the calibration work piece is illuminated from three different lighting directions.

27. The method according to claim 20, wherein calibration is completed before inspection of the surface segment, said calibration comprising the steps of:
   a. introducing a calibration work piece with defined, uniform and known surface attributes,
   b. illuminating the surface segment of a calibration unit with a required light source,
   c. capturing the reflected light from the surface segment of the calibration unit by means of a light sensor,
   d. establishing difference values based on actual reflection values and theoretical values due to the known surface attributes of the calibration work piece, and
   e. storing the difference values as correction values for successive inspections.

28. The method according to claim 20, wherein the one or more lenses has a number equaling two lenses.

* * * * *